United States Patent [19]

Baichwal et al.

[11] Patent Number: 5,128,143

[45] Date of Patent: * Jul. 7, 1992

[54] SUSTAINED RELEASE EXCIPIENT AND TABLET FORMULATION

[75] Inventors: Anand R. Baichwal, Poughkeepsie, N.Y.; John N. Staniforth, Bath, England

[73] Assignee: Edward Mendell Co., Inc., Patterson, N.Y.

[*] Notice: The portion of the term of this patent subsequent to Feb. 19, 2008 has been disclaimed.

[21] Appl. No.: 491,189

[22] Filed: Mar. 9, 1990

Related U.S. Application Data

[63] Continuation-in-part of Ser. No. 246,368, Sep. 19, 1988, Pat. No. 4,994,276.

[51] Int. Cl.$^5$ .......................... A61K 9/16; A61K 9/20; A61K 9/26
[52] U.S. Cl. ................................. 424/464; 424/439; 424/440; 424/465; 424/468; 424/469; 424/470; 424/488; 424/499; 424/500; 469/470; 469/488; 469/499; 469/555; 514/960; 514/965
[58] Field of Search ............... 424/464, 465, 468, 469, 424/470, 484, 488, 485

[56] References Cited

U.S. PATENT DOCUMENTS

| | | | |
|---|---|---|---|
| 2,993,836 | 7/1961 | Nash et al. | 167/82 |
| 3,074,852 | 1/1963 | Mayron | 167/82 |
| 3,079,303 | 2/1963 | Raff et al. | 167/82 |
| 3,133,863 | 5/1964 | Tansey | 424/465 |
| 3,147,187 | 9/1964 | Playfair | 167/182 |
| 3,456,049 | 7/1969 | Hotko et al. | 424/22 |
| 3,388,041 | 6/1968 | Gans et al. | 167/182 |
| 3,627,583 | 12/1971 | Troy et al. | 127/29 |
| 3,629,393 | 12/1971 | Nakamoto | 424/22 |
| 3,639,169 | 12/1971 | Broeg et al. | 167/82 |
| 3,726,690 | 4/1973 | Schuppner, Jr. | 99/139 |
| 3,728,445 | 5/1973 | Bardani | 424/22 |
| 3,773,920 | 11/1973 | Nakamoto et asl. | 424/19 |
| 3,836,618 | 9/1974 | Stevens | 264/101 |
| 3,864,469 | 2/1975 | Reiser et al. | 424/22 |
| 3,950,508 | 4/1976 | Mony et al. | 424/19 |
| 3,963,832 | 6/1976 | Hashimoto et al. | 424/49 |
| 4,013,820 | 3/1977 | Farhadieh et al. | 536/64 |
| 4,072,535 | 8/1977 | Short et al. | 424/22 |
| 4,167,558 | 9/1979 | Sheth et al. | 424/22 |
| 4,259,314 | 3/1981 | Lowey | 424/19 |
| 4,308,251 | 12/1981 | Dunn et al. | 424/19 |
| 4,361,545 | 11/1982 | Powell et al. | 424/19 |
| 4,389,393 | 10/1983 | Schor et al. | 424/19 |
| 4,424,235 | 1/1984 | Sheth et al. | 424/72 |
| 4,439,453 | 6/1984 | Vogel | 424/22 |
| 4,525,345 | 6/1985 | Dunn et al. | 424/22 |
| 4,542,011 | 9/1985 | Gleixner | 424/16 |
| 4,556,678 | 12/1985 | Hsiao | 514/652 |
| 4,590,062 | 5/1986 | Jang | 424/19 |
| 4,623,394 | 11/1986 | Nakamura et al. | 106/122 |
| 4,692,337 | 9/1987 | Ukigaya et al. | 424/469 |
| 4,695,463 | 9/1987 | Yang et al. | 424/488 |
| 4,695,467 | 9/1987 | Uemura et al. | 424/502 |
| 4,698,101 | 10/1987 | Koivurinta | 424/453 |
| 4,704,285 | 11/1987 | Alderman | 424/468 |
| 4,717,713 | 1/1988 | Zatz et al. | 514/2 |
| 4,755,389 | 1/1988 | Jones et al. | 514/2 |
| 4,762,702 | 8/1988 | Gergely et al. | 424/300 |
| 4,803,077 | 1/1989 | Mitsuhashi et al. | 424/440 |
| 4,829,056 | 5/1989 | Sugden | 424/464 |

FOREIGN PATENT DOCUMENTS 0180364  5/1986  European Pat. Off. .
0234670  9/1987  European Pat. Off. .

(List continued on next page.)

OTHER PUBLICATIONS

Satiaxane Food-Grade Xanthan Gum published by Satia.

(List continued on next page.)

*Primary Examiner*—Thurman K. Page
*Assistant Examiner*—James M. Spear
*Attorney, Agent, or Firm*—Steinberg & Raskin

[57] ABSTRACT

A slow release pharmaceutical excipient of an inert diluent and a hydrodrophilic material including xanthan gum and a galactomannan gum capable of cross-linking the xanthan gum in the presence of aqueous solutions.

24 Claims, 9 Drawing Sheets

FOREIGN PATENT DOCUMENTS

| | | |
|---|---|---|
| 8400104 | 1/1984 | PCT Int'l Appl. . |
| 8700044 | 1/1987 | PCT Int'l Appl. . |
| 8705212 | 9/1987 | PCT Int'l Appl. . |
| 1097807 | 12/1967 | United Kingdom . |
| 2178658 | 2/1987 | United Kingdom . |
| 2188843 | 10/1987 | United Kingdom . |

OTHER PUBLICATIONS

Hydrocolloids a Publication by Mero Rousselot Satia.

Xanthan Gum/Keltrol Kaltan a Natural Biopolysaccharide for Scientific Water Control.

Formulating for Controlled Release With Methocel Cellulose Ethers, the Dow Chemical Company, 1987.

H. M. Ingani et al., 6th Pharmaceutical Technology Conference, Volume II, pp. 459–460, Canterbury, England 1987.

Pharm. Ind., vol. 42, No. 6, 1980, Georgakopoulos et al., "Locust Bean Gum as Granulating and Binding Agent for Tablets".

SUSTAINED RELEASE EXCIPIENT AND TABLET FORMULATION

This application is a continuation-in-part of U.S. application Ser. No. 246,368, filed Sep. 19, 1988, now U.S. Pat. No. 4,994,276.

FIELD OF THE INVENTION

The present invention relates to a sustained release pharmaceutical excipient product which can be blended with a wide range of therapeutically active medicaments and tableted.

BACKGROUND OF THE INVENTION

Many attempts have been made in the pharmaceutical art to provide a method by which therapeutically active medicaments can be directly tableted or mixed with a direct compression vehicle and thereafter directly tableted.

Very few therapeutically active medicaments can be directly tableted due to unacceptable flow characteristics and compressibility factors of the crystalline or powdered medicament, and also due to the small amounts of medicament needed to provide the desired effect. Therefore, it is a common practice to use an inert ingredient, i.e., excipients, diluents, fillers, binders and the like, such that the combination of the same with the medicament provides a material which can be directly compressed into tablets. In order to provide a directly compressible product, these excipients must have certain physical properties, including flowability, sufficient particle size distribution, binding ability, acceptable bulk and tap densities, and acceptable dissolution properties in order to release the medicament upon oral administration.

U.S. Pat. No. 3,639,169 (Broeg et al.) discloses one such direct compression vehicle for a therapeutically active medicament which consists of an insoluble or soluble diluent such as lactose dispersed in a matrix of a hydrophilic hydratable high polymer such as hydrophilic polysaccharides, hydrocolloids or proteinaceous materials. The polymer, diluent and water are mixed and the resulting dispersion is dried, forming a film. The cooled film is fragmented, ground to the desired particle size and then blended with a desired medicament.

In another method disclosed in U.S. Pat. No. 3,079,303 (Raff et al.), a granular excipient for making tablets is prepared by spray drying a slurry of 50%-98% filler, 1%-50% disintegrant, and 1%-50% binder. A medicament is then added to the excipient and the finished product is tableted.

It has become desirable to provide pharmaceutical formulations which utilize slow release profiles, an objective not contemplated in Broeg et al., Raff et al. or other similar prior art. The advantages of slow release products are well known in the pharmaceutical field and include the ability to maintain a desired blood level over a longer period of time while increasing patient compliance by reducing the number of administrations necessary to achieve the same.

Slow release excipients have been developed which attain their goals by a wide variety of methods. For instance, U.S. Pat. No. 3,629,393 (Nakamoto) utilizes a three-component system to provide slow release tablets in which granules of an active ingredient with a hydrophobic salt of a fatty acid and a polymer are combined with granules of a hydrocolloid and a carrier and granules of a carrier and an active or a buffering agent and then directly compressed into tablets. U.S. Pat. No. 3,728,445 (Bardani) discloses slow release tablets formed by mixing an active ingredient with a solid sugar excipient, granulating the same by moistening with a cellulose acetate phthalate solution, evaporating the solvent, recovering the granules and compressing under high pressure. These disclosures concentrate their attention to the type and combination of polymers and/or gums used, and processes for mixing the same, and therefore have not provided a directly compressible form of gums/polymers and adjuvants which can be used for a wide range of medicaments.

Other slow release excipients are disclosed in the prior art which are directed to particular therapeutically active medicaments.

In one such disclosure, U.S. Pat. No. 3,456,049 (Hotko et al.), a slow release benzothiadiazine diuretic tablets are prepared by mixing a fatty substance such as hydrogenated vegetable oil, alginic acid, a granulating liquid, a potassium salt and the benzothiadiazine. The wet mass is screened, dried, and then compressed into tablets. Similarly, U.S. Pat. No. 4,692,337 (Ukigaya et al.) provides a slow release excipient for theophylline which utilizes 5–200 parts of ethyl cellulose for each 100 parts theophylline, and optionally contains a filler such as lactose or a lubricant. The ingredients are mixed and compression molded into tablets. In yet another example, U.S. Pat. No. 4,308,251 (Dunn et al.), a sustained release aspirin formulation in which 0.8–1.6 percent of a release controlling agent (cellulose acetate phthalate) and 1.0–7.5 percent of an erosion-promoting agent (corn starch) by weight per tablet. A wet granular mass is formed, dried, reduced in particle size and compressed into tablets.

More recently, a great deal of attention in the pharmaceutical field has turned to the use of various hydrocolloid materials such as hydroxypropylmethyl cellulose in providing a slow release matrix for a variety of medicaments.

For example, U.S. Pat. No. 4,389,393 (Schor et al.) describes a slow release carrier base material of one or more hydroxypropylmethyl celluloses and up to 30% by weight of a mixture of methylcellulose, sodium carboxymethylcellulose and/or cellulose ether which can be mixed with a medicament and other needed ingredients such as binders, lubricants, etc. and then tableted. At least one of the hydroxypropylmethyl celluloses must have a methoxy content of 16%–24% by weight, a hydroxypropyl content of 4%–32% by weight, and a number average molecular weight of at least 50,000. The carrier base constitutes less than about one third of the weight of the solid unit dosage form.

It is acknowledged in Schor et al. that in order to make tablets using this carrier base, other ingredients which are conventional in tablet making must necessarily be included, such as binders, fillers, disintegrating agents and the like. Only the completed mixture, which includes these additional ingredients, possess sufficient properties to produce tablets having the necessary hardness and low level of friability. Thus, the carrier base of the Schor et al. disclosure is not directed to the tableting aspects.

U S. Pat. No. 4,704,285 (Alderman) discloses solid slow release tablets containing 5%–90% hydroxypropyl cellulose ether, 5%–75% of an optional additional hydrophilic colloid such as hydroxypropylmethyl cellulose, an effective amount of an active medicament, and optional binders, lubricants, glidants, fillers, etc. The hydroxypropyl cellulose ether is in the form of a finely sized powder and provides a longer release pattern than identical compositions having coarser particles. However, Alderman acknowledges the necessity of the additional excipients in order to form an acceptable solid tablet, (i.e. fillers, binders, lubricants and glidants). In preferred embodiments, these excipients comprise from 63.5%-94% of the tablet.

The carrier bases which provide the slow release profiles in these disclosures can only be compressed into a tablet or a solid dosage form with the aid of other conventional tableting adjuvants such as binders and the like, and therefore contribute only to the slow release aspect of the final solid unit dosage form and not to the tableting aspects. In other words, in each of these disclosures it is necessary for to first determine the physical properties of the active medicament to be tableted and thereafter proceed through a series of trial and error experiments in order to determine the optimal amount of gums/polymers and other adjuvants to produce the right formulation which is free flowing and which can be compressed to a slow release solid dosage unit. This procedure is time intensive and costly.

Similarly, slow release excipients disclosed to date which incorporate virtually any synthetic polymer such as hydroxypropylmethylcellulose, methyl cellulose, polyvinylpyrollidone, and any natural gum such as acacia tragacanth, alginates, chitosan, xanthan, pectin and others to date have been mainly directed to the slow release aspect and do not satisfactorily address the tableting aspect. This is because these materials are not available in the necessary physical form that is essential for forming a solid unit dosage form.

The failure of slow release excipients such of the above to be regarded as to their tableting properties is due, for instance, to their necessarily very fine particle size, which property does not lend itself well to flowability. Also, hydroxypropylmethyl cellulose polymers and the like are not particularly good binding agents, a problem which is amplified when other poorly binding excipients or medicaments are included in a formulation. Thus, at higher percentages of such polymers in the final mixture, it becomes difficult if not impossible to provide a good flowing tablet formulation for direct compression without the use of further excipients, and experimentation.

The tableting aspect has been addressed, albeit unsatisfactorily, in U.S. Pat. No. 4,590,062 (Jang). Jang discloses a dry direct compressed slow release tablet containing from 0.01 to 95 parts by weight of an active ingredient combined with a matrix blend of 1-96 parts of a hydrophobic carbohydrate polymer and 4-99 parts of a wax, and a fatty acid material or neutral lipid. The tablets can be made by dry blending the active ingredient with the matrix blend and compressing. However, while this combination of ingredients can provide a directly compressible tablet, the formulator is still required to perform a great deal of experimentation to provide the correct release profile for the chosen medicament, given the wide range of wax (used for its binding and compacting properties) which can be included.

It is therefore an object of the present invention to provide a free-flowing directly compressible slow release excipient which can be used for a wide variety of therapeutically active medicaments.

It is another object of the present invention to provide an excipient which can be prepared by wet granulation to form controlled release tablets.

It is a further object of the present invention to provide an excipient having the properties set forth above which can be used with both relatively soluble and relatively insoluble therapeutically active medicaments.

It is a further object of the present invention to provide a free-flowing directly compressible slow release excipient which is relatively inexpensive to manufacture due to the lack of coatings and expensive equipment.

SUMMARY OF THE INVENTION

In accordance with the above-mentioned objectives, the present invention provides a slow release pharmaceutical excipient comprising from about 20 to about 70 percent or more by weight of a hydrophilic material comprising a heteropolysaccharide and a polysaccharide material capable of cross-linking the heteropolysaccharide in the presence of aqueous solutions, and from about 30 to about 80 percent by weight of an inert pharmaceutical filler. This excipient can be mixed with a wide range of therapeutically active medicaments and then directly compressed into solid dosage forms such as tablets. The tablets thus formed slowly release the medicament when ingested and exposed to gastric fluids. By varying the amount of excipient relative to the medicament, a slow release profile can be attained.

The heteropolysaccharide comprises from about 20 to about 80 percent and the polysaccharide material comprises from about 80 to about 20 percent by weight of the hydrophilic matrix. Preferably, the ratio of heteropolysaccharide to polysaccharide material is about 1:1.

In preferred embodiments, the heteropolysaccharide comprises xanthan gum or a derivative thereof.

In another preferred embodiment, the polysaccharide material comprises one or more galactomannans. Most preferably, the polysaccharide material comprises locust bean gum.

In yet another preferred embodiment, the inert pharmaceutical filler comprises lactose, dextrose, sucrose, sorbitol, xylitol, fructose or mixtures thereof.

The present invention also provides a slow release granulation for use as a directly compressible pharmaceutical excipient, comprising a heteropolysaccharide or a gum having similar properties and a polysaccharide material capable of cross-linking the heteropolysaccharide in the presence of water, the ratio of the heteropolysaccharide to the polysaccharide material being from about 1:1 to about 4:1.

The present invention also provides a slow release tablet for oral administration comprising (I) a hydrophilic material comprising (a) a heteropolysaccharide; or (b) a heteropolysaccharide and a cross-linking agent capable of cross-linking said heteropolysaccharide; or (c) a mixture of (a), (b) and a polysaccharide gum; and (II) an inert pharmaceutical filler comprising up to about 80 percent by weight of the tablet; and (III) an effective amount of a therapeutically active ingredient.

In addition, the present invention provides a method for providing a universal tableting excipient for controlled release of therapeutically active medicaments having varied solubilities in water, comprising determining the solubility of a therapeutically active medicament which is to be tableted; mixing an effective amount of said therapeutically active medicament with a premanufactured granulated slow release excipient comprising from about 20 to about 70 percent by weight of a hydrophilic material comprising a heteropolysaccharide and a polysaccharide capable of cross-linking said heteropolysaccharide in the presence of aqueous solutions, and up to 80 percent by weight of an inert pharmaceutical filler; providing a final mixed product having a ratio of said therapeutically active medicament to said hydrophilic material of about 1:3-7 depending upon the relative solubility of the medicament, amount of medicament needed (dose), the desired total weight of the tablet, the compression force used, etc.; and thereafter directly compressing the resulting blend to form a tablet. Generally, the more soluble the medicament, the greater the amount of hydrophilic material needed to produce a slow release of the medicament.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
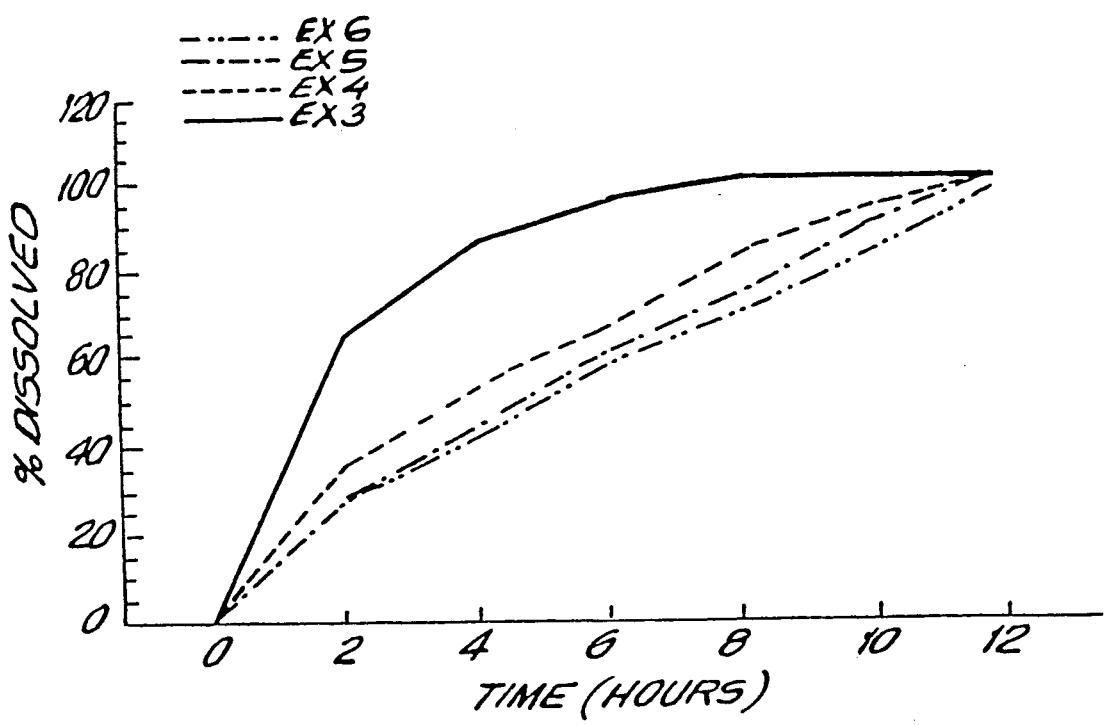
FIG. 1 is a graphical representation of the dissolution curves provided by Examples 3-6.

The excipients of the present invention have been preoptimized by providing an excipient product which may be mixed with a wide range of medicaments and directly compressed into solid dosage forms, without the aid of the usual pharmaceutical dry or wet binders, fillers, disintegrants, glidants etc. which must be added in prior art compositions to obtain an acceptable solid dosage form. Thus, the excipients of the present invention substantially overcome the need for conducting further experimentation needed to optimize release characteristics and tableting properties for a particular therapeutically active medicament.

In other words, the present invention provides a novel slow release excipient product which contains a combination of ingredients in preselected proportions to each other which provides a desired slow release profile for a wide variety of drugs. Thus, once the excipient product is admixed with an active medicament (and optional lubricant) in a ratio to the hydrophilic matrix in accordance with the present invention, the resulting mixture may be directly compressed into solid dosage forms.

Xanthan gum, the preferred heteropolysaccharide, is produced by microorganisms, for instance, by fermentation with the organism xanthomonas compestris. Most preferred is xanthan gum which is a high molecular weight ($>10^6$) heteropolysaccharide. Xanthan gum contains D-glucose, D-mannose, D-glucuronate in the molar ratio of 2.8:2.0:2.0, and is partially acetylated with about 4.7% acetyl. Xanthan gum also includes about 3% pyruvate, which is attached to a single unit D-glucopyromosyl side chain as a ketal. It dissolves in hot or cold water and the viscosity of aqueous solutions of xanthan gum is only slightly affected by changes in the pH of a solution between 1 and 11.

Other preferred heteropolysaccharides include derivatives of xanthan gum, such as deacylated xanthan gum, the carboxymethyl ether, and the propylene glycol ester.

The polysaccharide materials used in the present invention which are capable of cross-linking with the heteropolysaccharide include the galactomannans, i.e., polysaccharides which are composed solely of mannose and galactose. A possible mechanism for the interaction between the galactomannan and the heteropolysaccharide involves the interaction between the helical regions of the heteropolysaccharide and the unsubstituted mannose regions of the galactomannan. Galactomannans which have higher proportions of unsubstituted mannose regions have been found to achieve more interaction with the heteropolysaccharide. Hence, locust bean gum, which has a higher ratio of mannose to galactose, is especially preferred as compared to other galactomannans such as guar and hydroxypropyl guar.

Other polysaccharide gums may also be added to the hydrophilic material in addition to the above-mentioned ingredients. These additional ingredients comprise other polysaccharide gums which may or may not cross-link with the heteropolysaccharides such as the alginates, tragacanth, acacia, karaya, agar, pectins, carrageenan, hydroxypropylmethyl cellulose, hydroxypropyl cellulose, carboxymethyl cellulose, polyvinyl pyrrolidone, mixtures thereof, and the like.

Two steps which are generally required for gelation are the fast hydration of the macromolecules which comprise the hydrophilic material and thereafter the association of the molecules to form gels. Thus, two important properties of a hydrophilic gel matrix which are needed for application in a slow release system are the fast hydration of the system and a matrix having a high gel strength. These two important properties which are necessary to achieve a slow release hydrophilic matrix are maximized in the present invention by the particular combination of materials. In particular, heteropolysaccharides such as xanthan gum have excellent water wicking properties which provide fast hydration. On the other hand, the combination of xanthan gum with polysaccharides materials and the like which are capable of cross-linking the rigid helical ordered structure of the xanthan gum (i.e. with unsubstituted mannose regions in galactomannans) thereby act synergistically to provide a higher than expected viscosity (i.e., high gel strength) of the matrix.

Certain other polysaccharide gums, including alginic acid derivatives, hydrocolloids, etc. also are believed to act synergistically with xanthan gum to produce matrices having high gel strength. The combination of xanthan gum with locust bean gum with or without the other polysaccharide gums is especially preferred. However, the combination of any polysaccharide gums known to produce a synergistic effect when exposed to aqueous solutions may be used in accordance with the present invention. By synergistic effect it is meant that the combination of two or more polysaccharide gums produce a higher viscosity and/or faster hydration than that which would be expected by either of the gums alone. One example of a combination of polysaccharide gums which has been reported to exhibit such synergism in food products is kappa carrageenan and a galactomannan such as guar gum and/or locust bean gum. Additionally, the combination of propylene glycol alginate and sodium carboxymethylcellulose has also been reported to exhibit a synergistic effect as a stabilizer in fruit juices in U.S. Pat. No. 4,433,000. This list is not meant to be exclusive, and many other synergistic combinations will be readily apparent to those skilled in the art.

Mixtures of xanthan gum and locust bean gum in a ratio from about 20:1 to about 1:10 are disclosed in U.S. Pat. No. 3,726,690 (Schuppner) as being useful to minimize serum separation in amounts of 0.2%–0.6% by weight of acidified food products. In addition, mixtures of xanthan gum/locust bean gum are commercially available as Lygomme H96 from Satia and are recommended for uses such as syrup thickening, suspension of active components and emulsion stabilization.

In the present invention it has been discovered that the slow release properties of the tablets are optimized when the ratio of xanthan gum to polysaccharide material (i.e., locust bean gum, etc.) is about 1:1, although xanthan gum in an amount of from about 20 to about 80 percent or more by weight of the hydrophilic material provides an acceptable slow release product.

Upon oral ingestion and contact with gastric fluid, the slow release tablets prepared according to the present invention swell and gel to form a hydrophilic gel matrix from which the drug is released. The swelling of the matrix causes a reduction in the bulk density of the tablet and provides the buoyancy necessary to allow the gel mass to float on the stomach contents to provide a slow delivery of the medicament. The matrix, the size of which is dependent upon the size of the original tablet, can swell considerably and become obstructed near the opening to the pylorus. Since the medicament is dispersed throughout the tablet (and consequently throughout the gel matrix), a constant amount of drug can be released per unit time in vivo by dispersion or erosion of the outer portions of the matrix. This phenomenon is commonly referred to as a zero order release profile or zero order kinetics. The process continues, with the matrix remaining buoyant in the stomach, until substantially all of the medicament is released. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract. Moreover, the chemistry of the ingredients comprising the excipients of the present invention is believed to be similar to certain known muco adhesive substances such as polycarbophil. Muco adhesive properties are desirable for buccal delivery systems. Thus, it may be possible that the gel system could potentially loosely interact with the mucin in the gastrointestinal tract and thereby provide another mode by which a constant rate of delivery of the medicament is achieved. The above hypothesis is included for discussion purposes only and is not intended to limit the scope of the present invention.

These two phenomenons, i.e., buoyancy of the gel matrix and the mucoadhesive properties discussed above, are possible mechanisms by which the gel matrix of the present invention could interact with the mucin and fluids of the gastrointestinal tract and provide a constant rate of delivery of the medicament. Other mechanisms are possible and therefore this hypothesis is not meant to limit the scope of the present invention.

Any generally accepted soluble or insoluble inert pharmaceutical filler (diluent) material can be used, including sucrose, dextrose, lactose, microcrystalline cellulose, xylitol, fructose, sorbitol, mixtures thereof and the like. However, it is preferred that a soluble pharmaceutical filler such as lactose, dextrose, sucrose, or mixtures thereof be used.

An effective amount of any generally accepted pharmaceutical lubricant, including the calcium or magnesium soaps may be added to the above-mentioned ingredients of the excipient at the time the medicament is added, or in any event prior to compression into a solid dosage form. Most preferred is magnesium stearate in an amount of about 0.5%–3% by weight of the solid dosage form.

The combination of the hydrophilic material (i.e., a mixture of xanthan gum and locust bean gum) with the inert diluent provides a ready to use product in which a formulator need only blend the desired active medicament and an optional lubricant with the excipient and then compress the mixture to form slow release tablets. The excipient may comprise a physical admix of the gums along with a soluble excipient such as compressible sucrose, lactose or dextrose, although it is preferred to granulate or agglomerate the gums with plain (i.e., crystalline) sucrose, lactose, dextrose, etc. to form an excipient. The granulate form has certain advantages including the fact that it can be optimized for flow and compressibility; it can be tableted, formulated in a capsule, extruded and spheronized with an active medicament to form pellets, etc.

The pharmaceutical excipients prepared in accordance with the present invention are preferably subjected to wet granulation before the medicament is added, although the ingredients of the present excipient can be held together by any agglomeration technique to yield an acceptable excipient product. In this technique, the desired amounts of the heteropolysaccharide, the polysaccharide material, and the inert filler are mixed together and thereafter a moistening agent such as water, propylene glycol, glycerol, alcohol or the like is added to prepare a moistened mass. Next, the moistened mass is dryed. The dried mass is then milled with conventional equipment into granules. Thereafter, the excipient product is ready to use.

The excipient is free-flowing and directly compressible. Accordingly, the excipient may be mixed in the desired proportion with a therapeutically active medicament and optional lubricant (dry granulation). Alternatively, all or part of the excipient may be subjected to a wet granulation with the active ingredient and thereafter tableted. The complete mixture, in an amount sufficient to make a uniform batch of tablets, is then subjected to tableting in a conventional production scale tableting machine at normal compression pressures, i.e. about 2000–16000 lbs/sq. in. However, the mixture should not be compressed to such a degree that there is subsequent difficulty in its hydration when exposed to gastric fluid.

One of the limitations of direct compression as a method of tablet manufacture is the size of the tablet. If the amount of active is high a pharmaceutical formulator may choose to wet granulate the active with other excipients to attain a decent size tablet with the right compact strength. Usually the amount of filler/binder or excipients needed in wet granulation is less than that in direct compression since the process of wet granulation contributes to some extent toward the desired physical properties of a tableting mix.

The average tablet size for round tablets is preferably about 500 mg to 750 mg and for capsule-shaped tablets about 750 mg to 1000 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec.

The ratio of medicament to the hydrophilic material is based in part upon the relatively solubility of the medicament and the desired rate of release. For instance, the ratio of medicament to hydrophilic material can be adjusted to yield a product wherein 50 percent of the medicament will dissolve in distilled water within about 3.5–5 hours if a 6–8 hour dosing preparation is desired. This is accomplished by providing a ratio of medicament to hydrophilic material of about 1:3–7 for a wide range of medicaments of varying solubilities. However, it would be obvious to one skilled in the art that by varying this proportion and/or the total weight of the tablet, etc., one can achieve different slow release profiles, and may extend the dissolution of some medicaments to about 24 hours. If the medicament is relatively insoluble, the ratio of medicament to hydrophilic material tends to be smaller, while if the medicament is relatively soluble, the ratio tends to be toward the greater end. By "relatively insoluble", it is meant that the medicament exhibits a solubility which is defined in the United States Pharmacopeia (USP) XXI, page 7 as requiring about 10–30 parts solvent for 1 part solute (described therein as "soluble"). An example of a medicament which is considered relatively insoluble for the purposes of the present invention is propranol hydrochloride, which has a solubility of about 1 gram in 20ml of water or alcohol. By "relatively soluble", it is meant that the medicament exhibits a solubility which is defined in the USP XXI, page 7 as requiring from about 1–10 parts solvent per 1 part solute (described therein as "freely soluble). Examples of medicaments which are considered relatively soluble for the purposes of the present invention include chlorpheniramine maleate, which has a solubility of 1 g in 4 ml of water or 10 ml of alcohol, and verapamil HCl. Examples of other medicaments which have solubilities falling within these approximate parameters may be determined from any number of sources such as the Solubility Reference Table found in the USP XXI, pages 1484–9.

The excipient product of the present invention is also contemplated for use in conjunction with insoluble medicaments. By "insoluble", it is meant that the medicament exhibits a solubility which is defined in the USP XXI, page 7 as requiring from about 30–1000 parts solvent per 1 part solute (described) therein as "sparingly soluble" and "slightly soluble"). In such circumstances, the excipient product will be acting to control the release of the medicament rather than necessarily slowing its release. An example of such an insoluble medicament is theophylline.

As previously mentioned, the excipient product of the present invention can be used in conjunction with a wide range of medicaments. Since precise dosing is not very critical in medicaments having a wide therapeutic window, the present invention is especially well-suited for the same. The therapeutic window is commonly defined as the difference between the minimum effective blood concentration and the maximum effective blood concentration and the toxic concentration of the medicament.

Variables which may affect the release rate and compressibility of tablets prepared with the excipient of the present invention are:

a) Drug to polymer ratio;
b) Method of incorporation of excipient (Method of granulation);
c) Amount of gum blend; and
d) Composition of gum mix.

Examples of such medicaments which can be used in accordance with the present invention include analgesics, antihistamines, decongestants, laxatives, antacids, vitamins, anti-infectives, anti-inflammatories, antibiotics, vasoconstrictors, vasodilators, psychotropics, stimulants including appetite suppressants, diuretics, anti-asthmatics, diuretics, anti-spasmodics, antidiarrheals, expectorants, mucolytics, cough suppressants, hypnotics, psychotropics, sedatives and others.

DETAILED DESCRIPTION OF THE PREFERRED EMBODIMENT

The following examples illustrate various aspects of the present invention. They are not to be construed to limit the claims in any manner whatsoever.

EXAMPLE 1

Preparation of Excipient

A slow release excipient according to the present invention is prepared as follows. First, 600 g of sucrose and 300 g of a mixture of xanthan gum and locust bean gum in approximately a 1:1 ratio, all in powder form having an average particle size of less than about 50 microns, are blended for two minutes in a granulator (i.e., a high speed mixer having a combination chopper/impeller). About 125 ml of water is added to the mixture until there is a sharp rise in the power consumed (about 2-3 minutes). The mixed product, which is now in the form of granules, is removed from the granulator and dried in a convection air-oven for 24 hours at a temperature of about 40° C.-60° C. The dried granulation is then passed through a 20 mesh screen. The product is now ready to be used as a slow release excipient which is suitable for direct compression with any active medicament to form a slow release tablet.

EXAMPLE 2

Dry Granulation

Slow release tablets according to the present invention are prepared as follows. The excipient of Example 1 is first blended with chlorpheniramine maleate for 10 minutes in a V-blender. Magnesium stearate is then added as a lubricant and the mixture is blended for an additional 5 minutes. The final composition of the mixture is about 87.5% of the excipient of Example 1, 12% chlorpheniramine maleate, and 0.5% magnesium stearate by weight.

The mixture is then compressed on a Stokes RB-2 rotary tablet press with sixteen stations, the target weight of the tablets being 100 mg and the crushing strength about 6-8 kgs.

EXAMPLE 3-15

Chlorpheniramine

Slow release chlorpheniramine maleate tablets are prepared according to the procedures set forth in Examples 1 and 2, except that the excipient formulation is varied such that the amount of hydrophilic material (for purposes of the present examples referred to as "gums") relative to the total amount of excipient is varied from 20%-50%. In each of Examples 3-15, the gums are xanthan gum/locust bean gum in approximately a 1:1 ratio. In Examples 3-8, the inert diluent is dextrose. In Examples 9-11, the inert diluent is sucrose. The inert diluent in Examples 12 and 13 is lactose, while in Examples 14 and 15 the inert diluent is a 50/50 mixture of lactose and dextrose. In each of Examples 3-15, the total weight of the tablets is 100 mg. The amount of chlorpheniramine maleate in each of these Examples is 12 mg except for Example 8, in which only 8 mg of the drug were incorporated.

In addition, comparative examples A and B are prepared. Example A is provided with an excipient comprising 30% hydroxypropylmethyl cellulose (grade K15M, available from Dow Chemical) and 70% dextrose. Example B as provided with an excipient comprising 30% hydroxypropylmethyl cellulose (grade K4M, available from Dow Chemical) and 70% dextrose. Comparative Examples A and B include 12 mg chlorpheniramine maleate in 100 mg tablets.

The granules are tested for tap and bulk density. In addition, the average particle size of the granulations is determined. The results are set forth in Table 1. Thereafter, the tablets produced in Examples 3-15 and comparative examples A and B are tested for dissolution in distilled water in an automated USP dissolution apparatus. The data is represented as the percentage of chlorpheniramine maleate released versus time. The results are provided in Table 2.

As can be seen from the dissolution data provided in Table 2, Examples 4-6, 11, 13 and 15 provide dissolution profiles whereby 50% of the drug dissolves in from about 3.5-5.5 hours. Examples 3, 8, 9, 10 and 14, on the other hand, produced dissolution profiles in which 50% of the drug dissolved within 3 hours. The difference in dissolution rates is related to the ratio of drug to the gums (in addition to other criteria, such as the total amount of gums in the tablet, etc.). In particular, dissolution of 50% of the drug in 3.5-5.5 hours is accomplished with drug/gums ratios of 1:2.2-3.8, while the shorter dissolution times are accomplished with a drug/gums ratios of 1:1.5-2.2. The slight overlap is due to the choice of inert diluents. Comparative Examples A and B (which included only a hydrocolloid as the gum and which did not include the heteropolysaccharide and cross-linking agent of the present invention) only provide a $T_{50}$ of 1-1.5 hours when utilizing comparable amounts of gum.

FIG. 1 is a graphical representation of the dissolution curves of Examples 3-6. As can be seen from the graph, the dissolution curves of Examples 4-6 in which the hydrophilic material (i.e., the gums) comprise from 30%-50% of the tablet, are similar, while Example 3 (20% gum) shows a much faster dissolution rate. The dissolution curves obtained when other diluents are used and the percentage of gums in the tablet changed also reflected this result.

TABLE 1

| | Chlorpheniramine Maleate Tablets (100 mg) | | | | | |
|---|---|---|---|---|---|---|
| Example | Diluent | Amt Drug | % Gums in Excipient | Ratio of Drug/Gums | Average Particle size (microns) | $D_B{}^2$ | $D_T{}^3$ |
| 3 | Dextrose | 12 mg | 20% | 1:1.5 | 239 | 0.61 | 0.72 |
| 4 | Dextrose | 12 mg | 30% | 1:2.2 | 217 | 0.64 | 0.76 |
| 5 | Dextrose | 12 mg | 40% | 1:3 | 187 | 0.64 | 0.78 |
| 6 | Dextrose | 12 mg | 50% | 1:3.6 | 202 | 0.57 | 0.70 |
| 7 | Dextrose | 12 mg | 33% | 1:2.4 | 206 | 0.60 | 0.72 |
| 8 | Dextrose | 8 mg | 33% | 1:3.8 | 206 | 0.60 | 0.72 |
| 9 | Sucrose | 12 mg | 20% | 1:1.5 | 265 | 0.59 | 0.70 |
| 10 | Sucrose | 12 mg | 30% | 1:2.2 | 252 | 0.58 | 0.71 |
| 11 | Sucrose | 12 mg | 40% | 1:3 | 209 | 0.59 | 0.75 |
| 12 | Lactose | 12 mg | 30% | 1:2.2 | 178 | 0.65 | 0.81 |
| 13 | Lactose | 12 mg | 40% | 1:3 | 185 | 0.62 | 0.76 |
| 14 | L/D[1] | 12 mg | 30% | 1:2.2 | 227 | 0.57 | 0.69 |
| 15 | L/D[1] | 12 mg | 40% | 1:3 | 221 | 0.59 | 0.70 |
| A | Dextrose | 12 mg | 30% | 1:2.2 | 226 | 0.43 | 0.56 |
| B | Dextrose | 12 mg | 30% | 1:2.2 | 233 | 0.46 | 0.58 |

[1]denotes a 50/50 mixture of lactose and dextrose
[2]denotes bulk density
[3]denotes tap density

TABLE 2

Chlorpheniramine Maleate Tablets (100 mg)
Dissolution Data (Distilled Water)

| Example | 2 hr | 4 hr | 8 hr | $T_{50}$[4] | $T_{90}$[5] |
|---------|------|------|------|-------------|-------------|
| 3  | 63.63 | 85.69 | 100   | 1-1.5   | 3.5-4   |
| 4  | 34.37 | 51.69 | 82.61 | 3.5-4   | 9-9.5   |
| 5  | 27.05 | 43.05 | 72.74 | 4.5-5   | 10.5-11 |
| 6  | 26.68 | 40.85 | 69.16 | 5-5.5   | 10.5-11 |
| 7  | 35.31 | 52.84 | 75.43 | 3-4     | 10-11   |
| 8  | 39.29 | 61.64 | 92.21 | 2-3     | 7-8     |
| 9  | 55.87 | 76.61 | 96.96 | 1.5-2   | 6-6.5   |
| 10 | 40.15 | 59.32 | 84.59 | 2.5-3   | 8.5-9   |
| 11 | 26.18 | 42.52 | 68.10 | 4-4.5   | 11-11.5 |
| 12 | 41.08 | 54.56 | 79.03 | 3-3.5   | 9-9.5   |
| 13 | 30.68 | 45.74 | 73.26 | 4.5-5   | 10-10.5 |
| 14 | 43.77 | 68.11 | 100   | 2-2.5   | 6-6.5   |
| 15 | 27.17 | 42.10 | 70.34 | 5.5     | 10.5-11 |
| A  | 59.55 | 82.44 | 95.44 | 1-1.5   | 5.5-6   |
| B  | 69.44 | 95.22 | 100   | 1-1.5   | 2.5-3   |

[4] denotes the time needed for 50% of the medicament to be released
[5] denotes the time needed for 90% of the medicament to be released.

EXAMPLES 16-19

Propranol

Slow release propranolol hydrochloride tablets are prepared according to the procedures set forth in Examples 1 and 2, except that the excipient formulation is varied such that the amount of hydrophilic material (referred to as "gums") relative to the total amount of excipient is varied between 40% and 50% and the total weight of the tablets varied from 200-350 mg. In each of Examples 16-19, the gums are xanthan gum/locust bean gum in approximately a 1:1 ratio and the amount of propranol hydrochloride is 20 mg. In Example 16, the inert diluent is lactose. In Example 17, the inert diluent is a 50/50 mixture of lactose and dextrose. Finally, in Examples 18 and 19, the inert diluent is dextrose and sucrose, respectively.

The granulations which are produced are tested for tap and bulk density. In addition, the average particle size of the granulations are determined. The results are set forth in Table 3. Thereafter, the tablets produced are tested for dissolution in distilled water in a USP dissolution apparatus which is automated. The data is represented as the percentage of propranol hydrochloride released versus time. The results are provided in Table 4.

As can be seen by the dissolution data provided in Table 4, each of Examples 16-19 provided a dissolution profile in which 50% of the drug is released in 8.5 to 10 hours. Once again, the dissolution rates are related to the ratio of drug to gums, with slight variances due to the choice of inert diluent. The importance of the total weight of the tablet in affecting the drug/gums ratio is also shown.

TABLE 3

Propranolol Hydrochloride Tablets

| Example | Diluent | % Gums in Excipient | Total Weight of Tablet | Average Particle size (microns) | Ratio of Drug/Gums |
|---------|---------|---------------------|------------------------|---------------------------------|--------------------|
| 16 | Lactose  | 40% | 350 mg | 185 | 1:6.6 |
| 17 | L/D      | 40% | 350 mg | 221 | 1:6.6 |
| 18 | Dextrose | 50% | 225 mg | 202 | 1:5   |
| 19 | Sucrose  | 40% | 200 mg | 209 | 1:3.6 |

TABLE 4

Propranolol Hydrochloride Tablets
Dissolution Data (Distilled Water)

| Example | 2 hr | 4 hr | 8 hr | $T_{50}$ | $T_{90}$ |
|---------|------|------|------|----------|----------|
| 16 | 11.35 | 19.55 | 37.55 | 10    | 15-15.5 |
| 17 | 13.40 | 22.05 | 47.40 | 8.50  | 16      |
| 18 | 14.10 | 22.29 | 43.12 | 9-9.5 | 15-15.5 |
| 19 | 18.40 | 27.67 | 45.88 | 9     | 15      |

Figure 2:
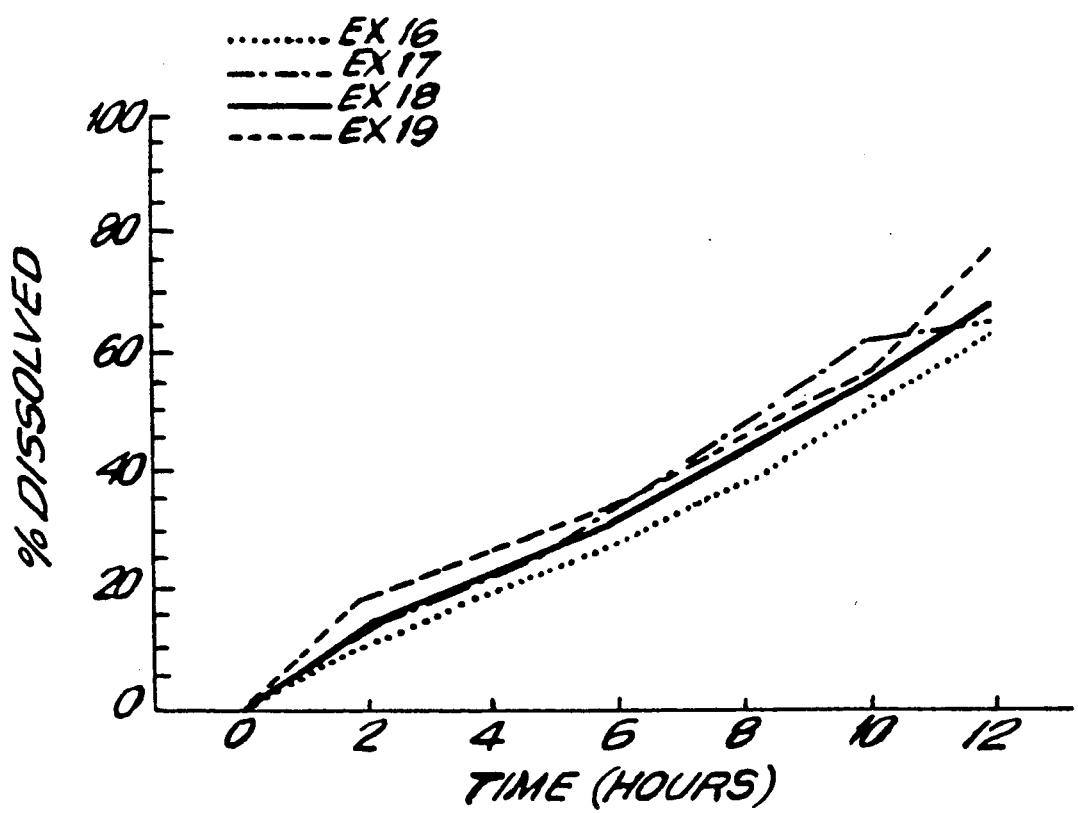
FIG. 2 is a graphical representation of the dissolution curves provided by Examples 16-19.

FIG. 2 is a graphical representation of the dissolution curve obtained with Examples 16-19.

EXAMPLES 20-28

Hydrophilic Material

Slow release propranolol tablets are prepared according to the procedures set forth in Examples 1 and 2 which illustrate various aspects of the present invention, including the addition of additional polysaccharide gums to the xanthan/locust bean gum mixture, and variances in the ratio of xanthan gum to locust bean gum. In Examples 20-22, the relative percentages of xanthan gum to locust bean gum are about 0/100, 25/75 and 75/25, respectively. In Examples 23 and 24, 50% of the hydrophilic matrix is propylene glycol alginate (PGA) and 50% is xanthan gum/locust bean gum in a 1:1 ratio. Examples 25 and 26 are similar to Example 23, except that the propylene glycol alginate is replaced with hydroxypropylmethyl cellulose 15M and 100M, respectively (both grades commercially available from Dow Chemical). Example 27 is also similar to Example 23, except that the propylene glycol alginate is replaced with sodium alginate. In Example 28, the excipient includes only xanthan gum. In each of Examples 20-28, the inert diluent is dextrose. To the excipient mixture, 20 mg propranolol hydrochloride is added. The tablets produced in each of Examples 20-27 weigh 350 mg.

In Comparative Example C, the excipient is 30% hydroxypropylmethyl cellulose and 70% dextrose by weight. The tablets of Comparative Example C also weighs 350 mg and includes 20 mg of propranolol hydrochloride. Table 5 sets forth the gums used in Examples 20-28 and Comparative Example C.

The dissolution of the tablets of Examples 20-28 and Comparative Example C is then tested in distilled water in an automated USP dissolution apparatus. The results are provided in Table 6.

TABLE 5

| | % Gums in Hydrophilic Material | | | | |
|---------|---------|-------------------|-----|------|-------------|
| Example | Xanthan | Locust Bean Gum | PGA | HPMC | Na Alginate |
| 20 | —    | 100 | —   | —    | —   |
| 21 | 25   | 75  | —   | —    | —   |
| 22 | 75   | 25  | —   | —    | —   |
| 23 | 25   | 25  | 50% | —    | —   |
| 24 | 25   | 25  | 50% | —    | —   |
| 25 | 25   | 25  | —   | 50%  | —   |
| 26 | 25   | 25  | —   | 50%  | —   |
| 27 | 25   | 25  | —   | —    | 50% |
| 28 | 100% | —   | —   | —    | —   |
| C  | —    | —   | —   | 100% | —   |

TABLE 6

Dissolution of Propranolol Hydrochloride
(350 mg tablets, 20 mg drug)

| Example | % Gums in Excipient | Ratio of Drug/Gums | 2 hr | 4 hr | 8 hr | $T_{50}$ | $T_{90}$ |
|---|---|---|---|---|---|---|---|
| 20 | 30% | 1:5 | 32.13 | 46.06 | 62.06 | 4.5-5 | 18+ |
| 21 | 40% | 1:6.5 | 22.54 | 30.71 | 45.96 | 8.5-9 | 16-16.5 |
| 22 | 40% | 1:6.5 | 12.9 | 22.75 | 50.05 | 8 | 12.5-13 |
| 23 | 30% | 1:5 | 23.35 | 39.05 | 75.70 | 5-5.5 | 9.5-10 |
| 24 | 40% | 1:6.5 | 20.12 | 32.79 | 64.17 | 6-6.5 | 11-11.5 |
| 25 | 30% | 1:5 | 37.54 | 50.04 | 65.00 | 4 | 15.5-16 |
| 26 | 30% | 1:5 | 32.71 | 41.79 | 54.88 | 6-6.5 | 18 |
| 27 | 30% | 1:5 | 25.12 | 44.38 | 100 | 4-4.5 | 6.5-7 |
| 28 | 30% | 1:5 | 17.38 | 31.00 | 59.88 | 6-6.5 | 11-11.5 |
| C | 30% | 1:5 | 52.25 | 74.85 | 94.85 | 1.5-2 | 7 |

Figure 3:
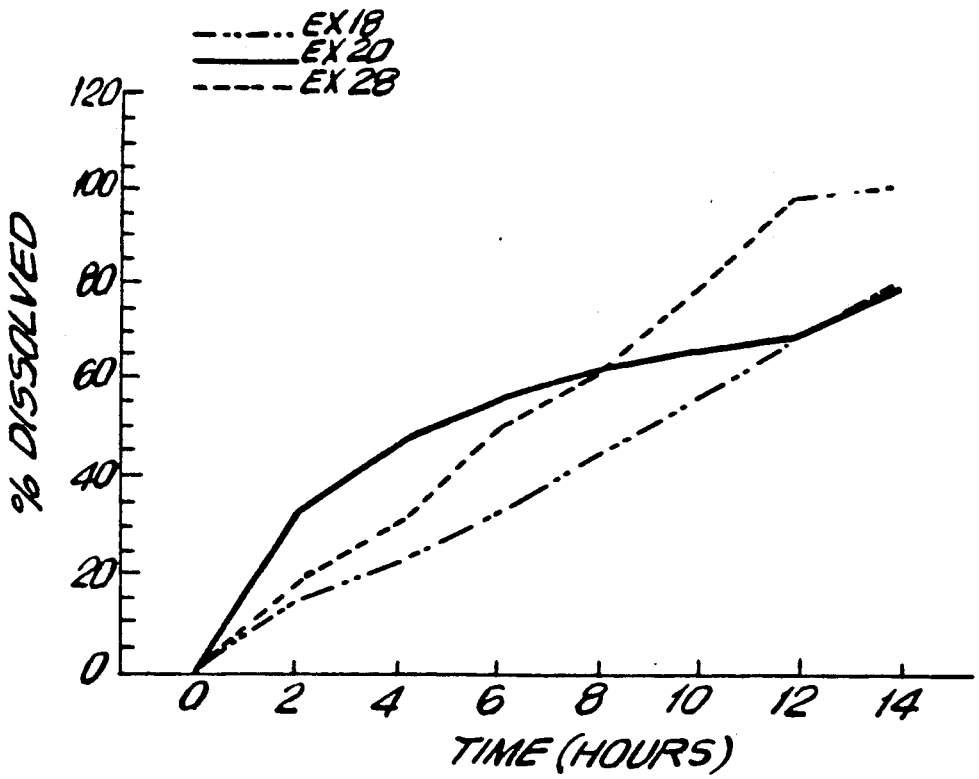
FIG. 3 is a graphical representation of the dissolution curves provided by Examples 18,20 and 28.

FIG. 3 is a graphical representation of the dissolution curves provided by Example 18 (xanthan gum/locust bean gum in a 1:1 ratio), Example 20 (100% locust bean gum), and Example 28 (100% xanthan gum). From the graph, it may be seen that the $T_{50}$ for Example 28 was longer than that for Example 20. The $T_{90}$ for Example 28, however, was shorter than that for Example 20. This result may be due to the fact that xanthan gum wets quicker than locust bean gum (thereby providing a quicker forming gel) but does not have as good gel strength as locust bean gum. The combination of xanthan gum/locust bean gum provides an excipient which both wets quickly and has a high gel strength. The $T_{50}$ provided by Example 18 is longer than either Example 20 or 28. The $T_{90}$ of Example 18 also reflects the improved gel strength obtained by the combination of the gums over xanthan gum alone.

Figure 4:
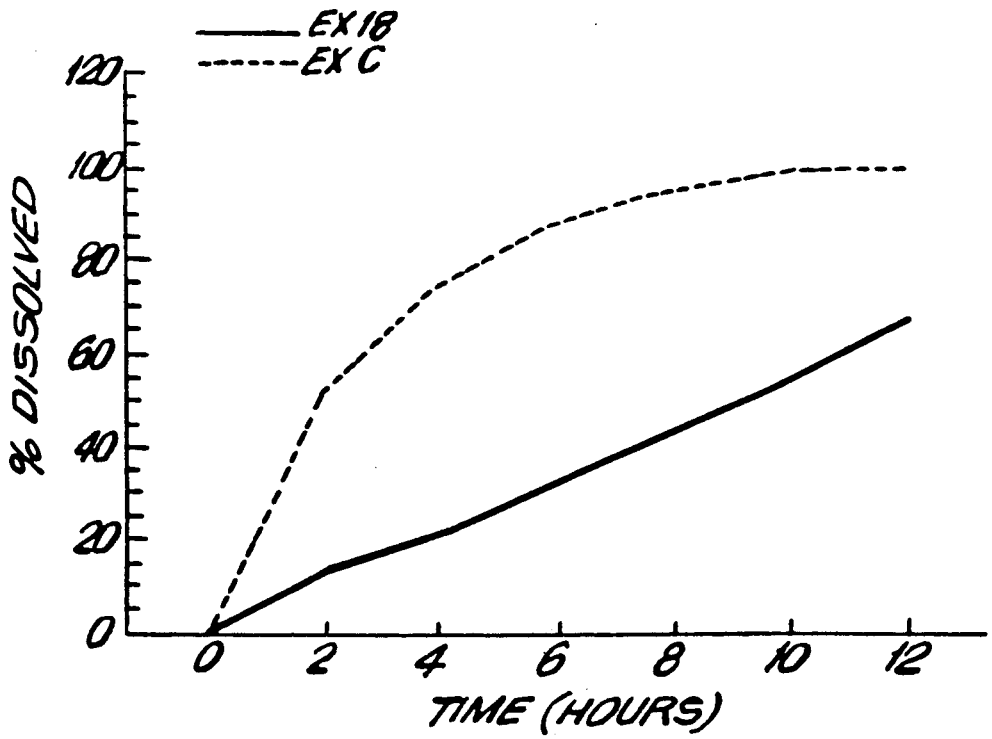
FIG. 4 is a graphical representation of the dissolution curve provided by Example 18 as compared to Comparative Example C.

FIG. 4 is another graphical representation showing the dissolution curve of Example 18 as compared to Comparative Example C (gum is hydroxypropylmethyl cellulose). This graph shows the synergistic effect of the combination of xanthan gum/locust bean gum as compared to a prior art hydrophilic gel matrix forming agent. One possible explanation for this phenomenon is that hydroxypropylmethyl cellulose does not wet as quickly nor form a gel matrix which is as strong as the gums used in Example 18, and therefore does not provide a sufficient slow release profile.

EXAMPLES 29-31 pH of the Environment

Propranolol hydrochloride tablets are prepared according to the procedures set forth in Examples 1 and 2. The tablets of Examples 29-31 have a total weight of 350 mg, of which 20 mg is the drug. The excipient comprises 40% gums (xanthan gum/locust bean gum in a 1:1 ratio) and 60% of an inert diluent (lactose). The drug/gums ratio is about 1:6.5.

In Example 29, the dissolution of the tablets was measured in an aqueous solution having a pH of 6.8. In Example 30, the dissolution of the tablets was measured in distilled water (pH=7). In Example 31, the dissolution of the tablets was measured in an acidic solution having a pH of 2.

The tablets of Examples 29-31 are then tested to determine their dissolution rates in environments having varied pH's (distilled water, pH 2, pH 6.8). The results are shown in FIG. 5 which is a graphical representation of the percentage of dissolved drug over time.

Figure 5:
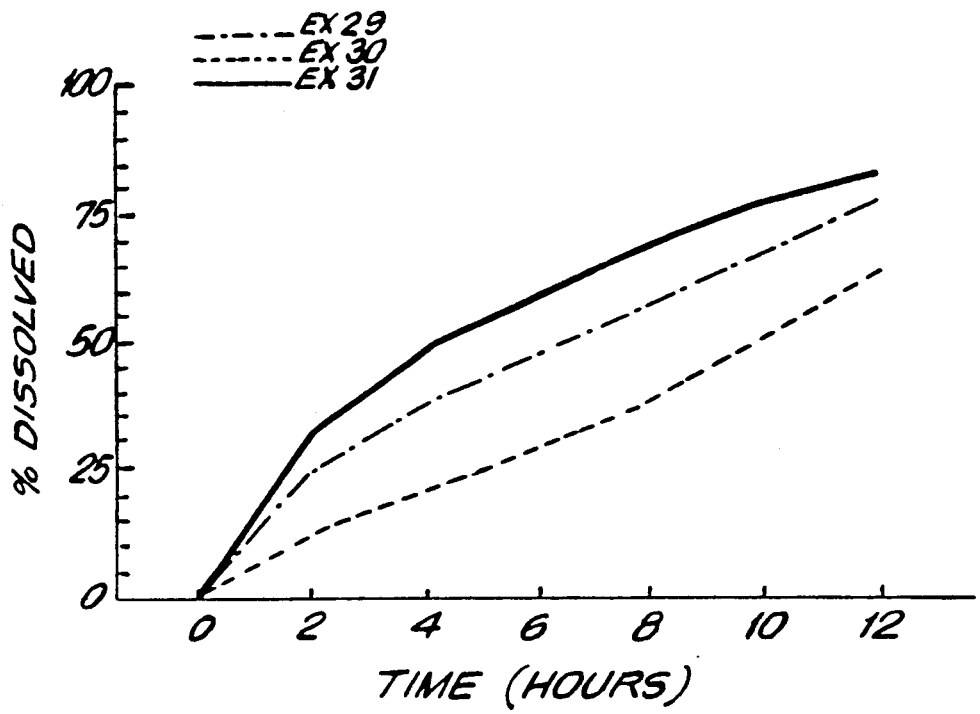
FIG. 5 is a graphical representation of the dissolution curve provided by Examples 29-31 (in different pH's)

As can be seen from FIG. 5, the dissolution times of the tablets in pH 6.8 and pH 2 are fairly close, while the dissolution time in unbuffered distilled water does not provide a similar profile. From the graphical representation, it may be concluded that the dissolution of the medicament (in this case propranolol) does not vary greatly in ionic solutions, even when the pH varies greatly, due to the relative insensitivity to pH of the excipients of the present invention.

EXAMPLES 32-36

Gum/total Excipient

Figure 6:
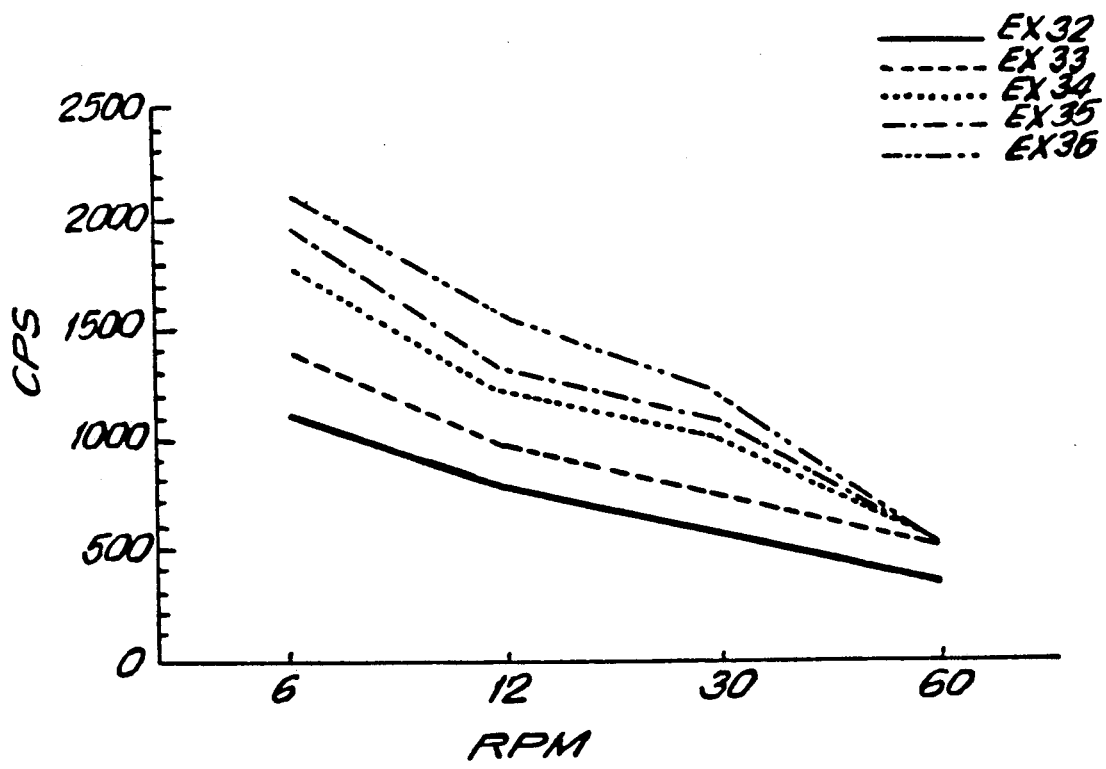
FIG. 6 is a graphical representation of the viscosities of Examples 32-36.

Slow release excipients are prepared according to procedures set forth in Example 1. The excipients of Examples 32-36 each include dextrose and xanthan gum/locust bean gum in a 1:1 ratio. The percentage of gums as compared to the total weight of the excipient in Examples 32-36 are 30%, 40%, 50%, 60% and 70%, respectively. The viscosities of the excipients are then determined at four different RPM's using a #2 spindle on a Brookfield viscometer. The results are shown in FIG. 6. As can be seen from the graph, the viscosity increases as the percentage of gum included in the excipient increases.

EXAMPLE 37

Preparation of Excipient

A slow release excipient according to the present invention is prepared as follows. First, 630 g of dextrose and 270 g of a hydrophilic material comprising 135 g of Xanthan gum and 135 g of locust bean gum, all in a powder form having an average particle size of less than 50 microns are blended for two minutes in a granulator (i.e., a high speed mixer having a combination chopper-/impeller). After pre-mixing, 100 ml of water is added until there is sharp rise in the power consumed (about 2-3 minutes). The mixed product, which is now in the form of granules, is removed from the granulator and dried in a convection air-oven for 24 hours at a temperature of about 40° C.-60° C. The dried granulation is then passed through a 20 mesh screen. The product is now ready to be granulated with an active, the result of which is suitable for compression to form a slow release tablet.

EXAMPLE 38

Wet Granulation

Verapamil HCl is a relatively soluble active ingredient which has a dose of about 240 mg in a sustained release tablet form.

In Example 38, the active ingredient (Verapamil) is granulated with the slow release excipient as follows. The excipient of Example 37 385 g is first blended with 115 g Verapamil HCl for two minutes in a granulator. After premixing, about 90 ml of water is added until there is a sharp rise in the power consumed by the granulator (about 2-3 minutes). The mixed product, which is now in the form of granules, is removed from the granulator and dried in a convection air-oven for 24 hours at a temperature of about 40° C.-60° C. The dried granulation is then passed through a 20 mesh screen. The final composition of the mixture is about 7.0% of the excipient of Example 37, and 23.0% Verapamil HCl.

The mixture is blended with hydrogenated vegetable oil for 5 minutes in a V-blender. Magnesium stearate is then added and the mixture is blended for an additional 5 minutes The final composition of the mixture is about 75.0% of the excipient of Example 37, 22.5% Verapamil HCl, 2.00% hydrogenated vegetable oil, and 0.500% magnesium stearate, by weight. The mixture is then compressed on a Stokes RB-2 rotary tablet press with sixteen stations. The average weight of the tablets produced is about 1067 mg and the crushing strength about 7-8 kgs. Each tablet contains about 240.08 Verapamil, 800.25 mg excipient of Example 37, 21.34 mg hydrogenated vegetable oil, and 5.34 mg magnesium stearate.

EXAMPLE 39

Dry granulation

The active ingredient is directly compressed with the slow release excipient of Example 37 to form sustained release tablets having approximately the same composition as those of Example 38 as follows. 300 g of the excipient of Example 37 is first blended with 90 g Verapamil HCl for 10 minutes in a V-blender. Hydrogenated vegetable oil is then added and the mixture is blended for 5 minutes. Magnesium stearate is then added and the mixture is blended for an additional 5 minutes. The final composition of the mixture is the same as in Example 38 and is tableted.

EXAMPLE 40

Mixed granulation

The active ingredient is granulated with 50% of the slow release excipient as follows. Half of the excipient of Example 37 is first blended with Verapamil HCl for 2 minutes in a granulator. Next, about 75 ml of water is added until there is a sharp rise in power consumed (usually 2-3 minutes). The mixed product, which is now in the form of granules, is removed from the granulator and dried in a convection air-oven for 24 hours at a temperature of about 40° C.-60° C. The dried granulation is then passed through a 20 mesh screen. The final composition is about 62.5% of the excipient of Example 37 and about 37.5% Verapamil HCl. The mixture is then blended with other half of excipient of Example 37 for 10 minutes in V-blender. Hydrogenated vegetable oil is then added and blended 5 minutes, magnesium stearate is then added and blended for an additional 5 minutes. The final composition of the mixture is the same as in Example 38 and Example 39 and is tableted.

EXAMPLES 41-43

Effect of Method of Incorporation

In Examples 41-43, the active ingredient (Verapamil HCl) is granulated with the slow release excipient according to the methods set forth in Examples 37-39 in order to compare the dissolution curves obtained.

In Example 41, the excipient is prepared according to the process set forth in Example 37 and is then blended with the active ingredient and tableted according to the process set forth in Example 38. In Example 42, the excipient is prepared according to the process set forth in Example 37 and is then blended with the active ingredient and tableted, according to the process set forth in Example 39. In Example 43, the excipient is prepared according to the process set forth in Example 37 and is then blended with the active ingredient and tableted according to the process set forth in Example 40.

In each of Examples 41-43, the tablets weigh about 1067 mg. The drug:gum ratio in each of Examples 41-43 is 1 1; and the locust bean gum (LBG) to xanthan gum (XG) ratio is 1:1.

Each tablet of Examples 41-43 contain about 240 mg verapamil HCl, about 800 mg excipient, about 21.3 mg hydrogenated vegetable oil, and about 5.3 mg magnesium stearate. Further information regarding Examples 41-43 is provided in Table 7 below.

TABLE 7

| Example | Drug:Gum Ratio | % Gum in Excipient | LBG:XG Ratio | T50 | T90 |
|---|---|---|---|---|---|
| 41 | 1:1 | 35 | 1:1 | 3.7 | 16.5 |
| 42 | 1:1 | 35 | 1:1 | 1.0 | 4.5 |
| 43 | 1:1 | 35 | 1:1 | 2.4 | — |

Figure 7:
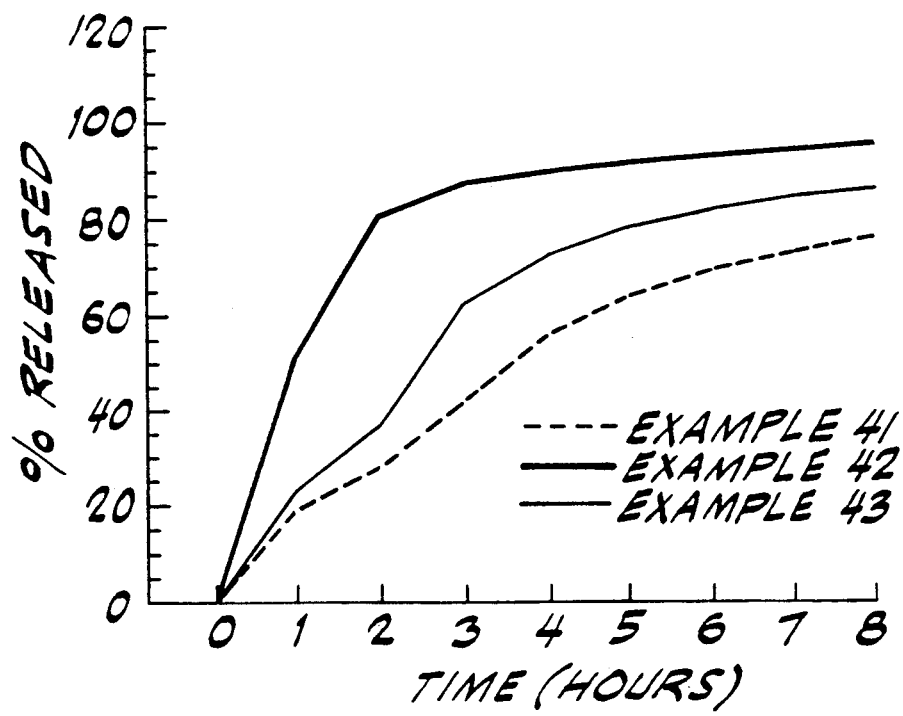
FIG. 7 is a graphical representation of the dissolution curves provided by Examples 41-43.

The tablets are tested in an automated USP dissolution apparatus, using distilled water at a volume of 1 liter and paddle method at 50 R.P.M. At 30 minute intervals the ultraviolet absorbance of filtered portions of solution are compared to a standard having a known concentration of USP Verapamil HCl in the same medium. The results are provided in FIG. 7.

EXAMPLES 44-46

Effect of Amount of Gum in Excipient

In Examples 44-46, the amount of gum in the excipient is varied in order to compare the dissolution curves of the active ingredient (verapamil HCl) obtained.

In each of Examples 44-46, the slow release excipient is prepared according to the process set forth in Example 37, except that the amount of gum in the excipient is varied. The slow release excipient obtained for each of Examples 44-46 is then blended with the active ingredient and tabletted according to the method set forth in Example 40.

The tablets of Example 44 weigh about 861.5 mg and contain about 240 mg verapamil HCl, about 600 mg excipient, about 17.2 mg hydrogenated vegetable oil, and about 4.3 mg magnesium stearate. The tablets of Example 45 weigh about 949.70 mg and contain about 240 mg verapamil HCl, about 686 mg excipient, about 19 mg hydrogenated vegetable oil, and about 4.70 mg magnesium stearate. The tablets of Example 46 weigh about 1066.60 mg and contain about 240 mg verapamil HCl, about 800 mg excipient, about 21.3 mg hydrogenated vegetable oil, and about 5.3 mg magnesium stearate. Further information regarding Examples 44-46 is provided in Table 8 below.

TABLE 8

| Example | Drug:Gum Ratio | % Gum in Excipient | LBG:XG Ratio | T50 | T90 |
|---|---|---|---|---|---|
| 44 | 1:1 | 40 | 1:1 | 2.9 | — |
| 45 | 1:1 | 35 | 1:1 | 2.4 | — |
| 46 | 1:1 | 30 | 1:1 | 1.2 | 3.3 |

Figure 8:
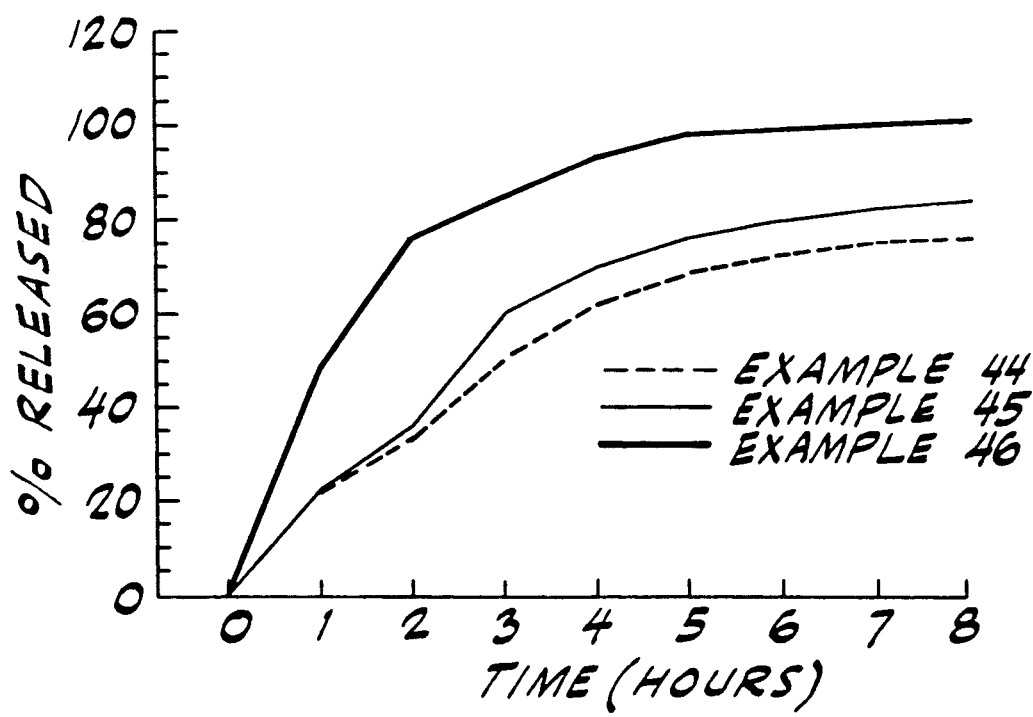
FIG. 8 is a graphical representation of the dissolution curves provided by Examples 44-46.

The tablets are then tested for dissolution in the same manner as in Examples 41-43. The results are provided in FIG. 8.

EXAMPLES 47-50

LBG:XG Ratio

In Examples 47-50, the ration of locust bean gum (LBG) to xanthan gum (XG) is varied and the dissolution curves compared.

In each of Examples 47-50, the slow release excipient is prepared according to the process set forth in Example 37, except that the LBG:XG ratio is varied. The slow release excipient obtained for each of Examples 47-50 is then blended with the active ingredient (verapamil HCl) and tabletted according to the process set forth in Example 40.

Each of the tablets of Examples 47-50 contain about 240 mg Verapamil HCl, about 738 mg excipient, about 20 mg hydrogenated vegetable oil, and about 5 mg magnesium stearate. Further information regarding Examples 47-50 is provided in Table 9 below.

TABLE 9

| Example | Drug:Gum Ratio | % Gum in Excipient | LBG:XG Ratio | T50 | T90 |
|---|---|---|---|---|---|
| 47 | 1:1 | 32.5 | 55:45 | 0.9 | 5.0 |
| 48 | 1:1 | 32.5 | 60:40 | 0.3 | 0.5 |
| 49 | 1:1 | 32.5 | 1:1 | 2.7 | 11.5 |
| 50 | 1:1 | 32.5 | 25:75 | 4.8 | 17.5 |

Figure 9:
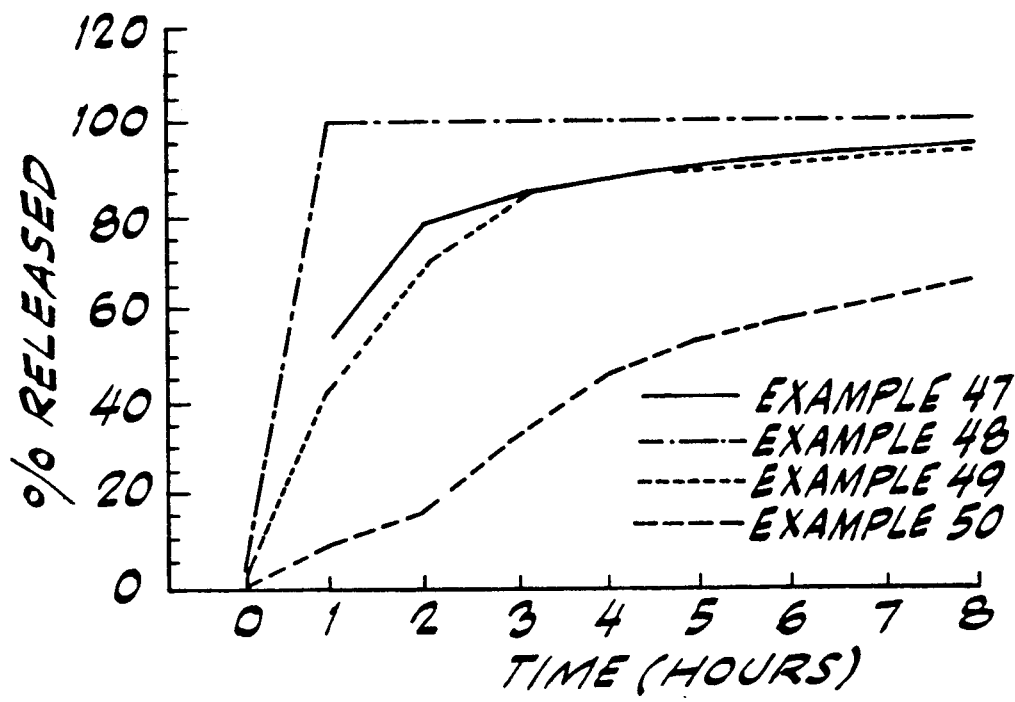
FIG. 9 is a graphical representation of the dissolution curves provided by Examples 47-50.

The tablets are then tested for dissolution in the same manner as in Examples 41-43. The results are provided in FIG. 9.

EXAMPLES 51-53

Drug:Gum Ratio

In Examples 51-53, the drug to gum ratio is varied and the dissolution curves compared.

In each of Examples 51-53, the slow release excipient is prepared according to Example 37 and is then blended with the active ingredient (Verapamil HCl) and tableted.

In Example 51, the tablets contain about 240 mg Verapamil, about 240 mg excipient, about 9.84 mg hydrogenated vegetable oil, and about 2.6 mg magnesium stearate. In Example 52, the tablets contain about 240 mg Verapamil, about 480 mg excipient, about 14.8 mg hydrogenated vegetable oil, and about 3.7 mg magnesium stearate. In Example 53, the tablets contain about 120 mg Verapamil, about 720 mg excipient, about 17.2 mg hydrogenated vegetable oil, and about 4.3 mg magnesium stearate. Further information regarding Examples 51-53 is set forth in Table 10 below.

TABLE 10

| Example | Drug:Gum Ratio | % Gum in Excipient | LBG:XG Ratio | T50 | T90 |
|---|---|---|---|---|---|
| 51 | 2:1 | 50 | 1:1 | 0.4 | 0.9 |
| 52 | 1:1 | 50 | 1:1 | 5.5 | — |
| 53 | 1:3 | 50 | 1:1 | — | — |

Figure 10:
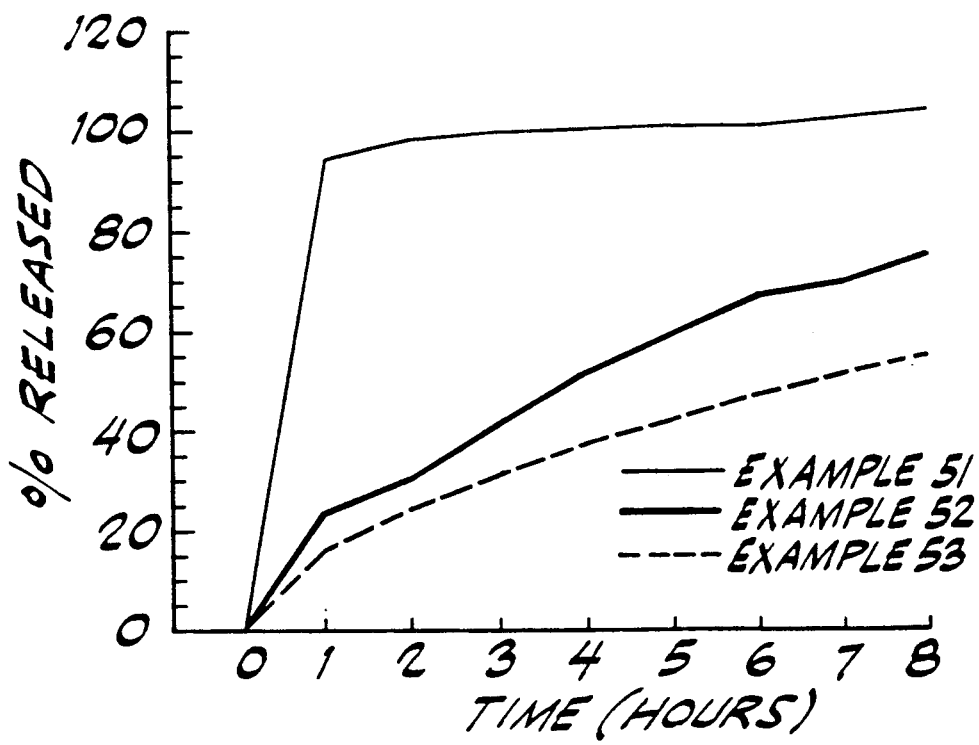
FIG. 10 is a graphical representation of the dissolution curves provided by Examples 51-53.

The tablets are then tested for dissolution in the same manner as in Examples 41-43. The results are provided in FIG. 10.

EXAMPLES 54-57

Tailoring to a Known Dissolution Curve

By varying the amount of gum, the LBG:XG ratio, the method of incorporation, or the drug:gum ratio, it is possible to closely match the dissolution profile of a different slow release formulation of the same drug. This is demonstrated in the following example.

First, a slow release excipient is prepared according to the process set forth in Example 37.

Figure 11:
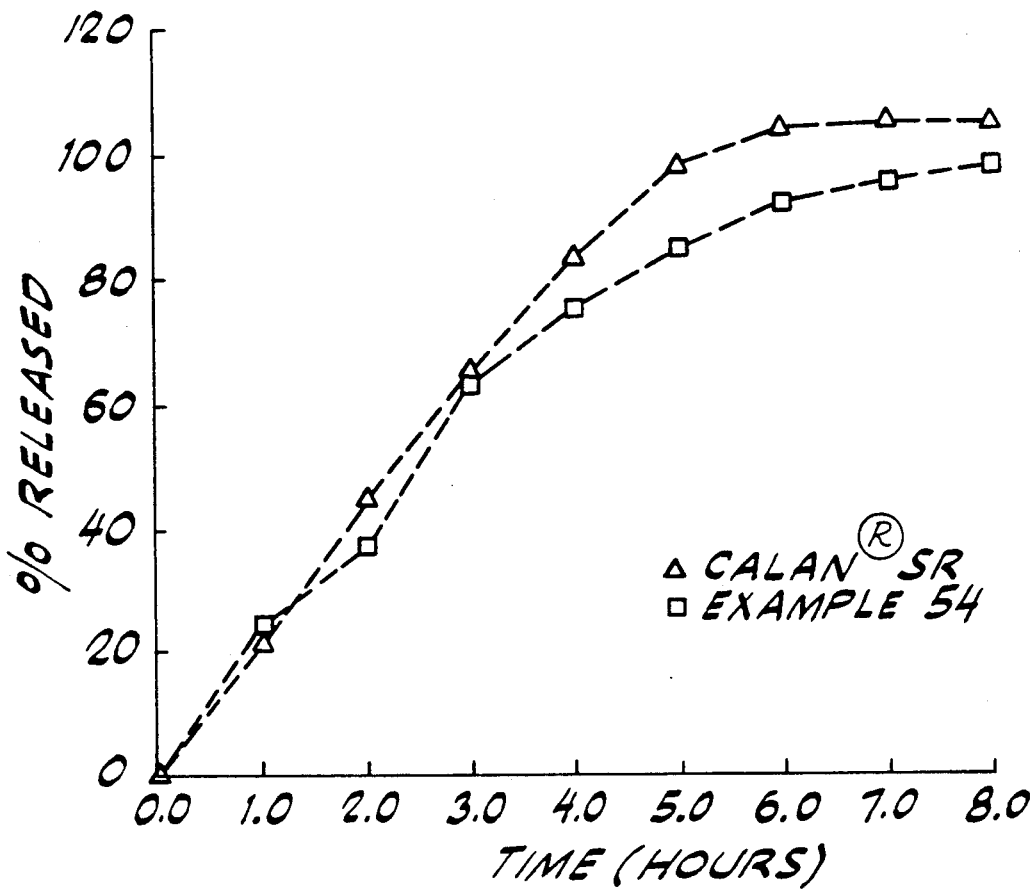
FIG. 11 is a graphical representation of the dissolution curves provided by Example 54 and Calan® SR.

In Example 54, the excipient is then blended with the active ingredient (verapamil HCl) and tableted according to the process set forth in Example 38. Each tablet contains about 260 mg Verapamil, about 780 mg excipient, about 21.3 mg hydrogenated vegetable oil, and about 5.3 mg magnesium stearate. The tablets are then tested for dissolution in the same manner as in Examples 41-43. As a comparative example, a Calan ® SR caplet (containing 240 mg Verapamil hydrochloride), available from G. D. Searle & Co., is similarly tested for dissolution. Further information regarding Example 54 is provided in Table 11 below, and the dissolution curves for Example 54 and Calan ® SR are provided in FIG. 11.

TABLE 11

| Example | Drug:Gum Ratio | % Gum in Excipient | LBG:XG Ratio | T50 | T90 |
|---|---|---|---|---|---|
| 18 | 1:0.9 | 50 | 1:1 | 2.4 | 5.9 |
| Calan ®SR | — | — | — | 2.3 | 4.5 |

Figure 12:
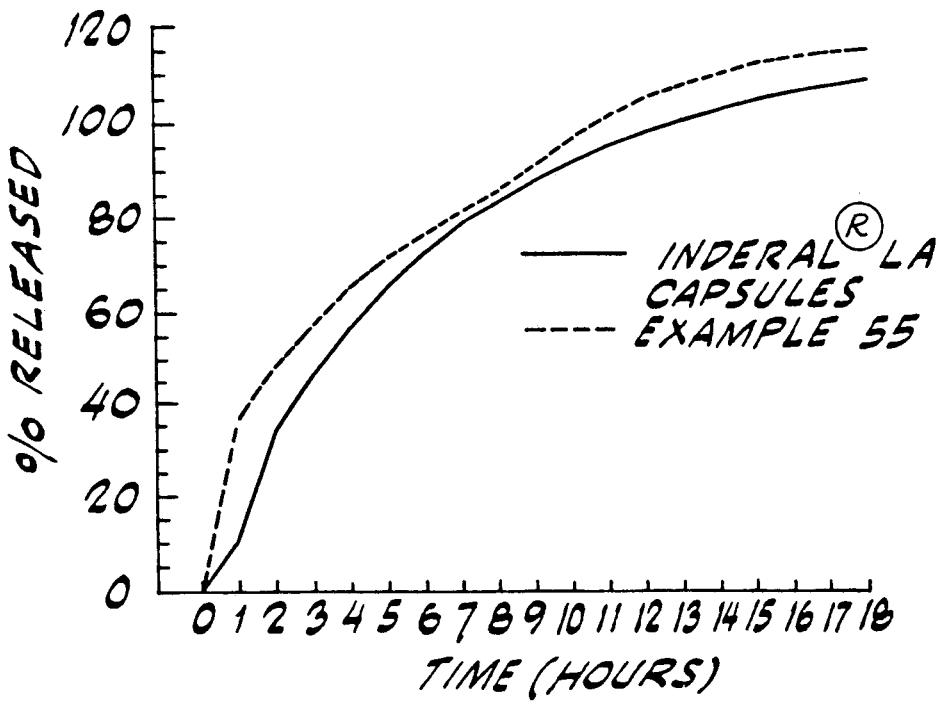
FIG. 12 is a graphical representation of the dissolution curves provided by Example 55 and Inderal® LA.

In Example 55, the excipient is blended with propranolol and tableted according to the process set forth in Example 38. Each tablet weighs about 820.5 mg, and contains 160 mg propranolol HCl, 16.4 mg hydrogenated vegetable oil, 4.10 mg magnesium stearate, and 640 mg excipient (containing 50% gums (XG:LBG in a 1:1 ration). The tablets are then tested for dissolution in the same manner as Examples 41-43 and the dissolution curve compared to a similarly tested tablet of Inderal ® LA (a slow release formulation containing 160 mg propranolol HCl; available from Wyeth-Ayerst. The results are proved in FIG. 12.

Figure 13:
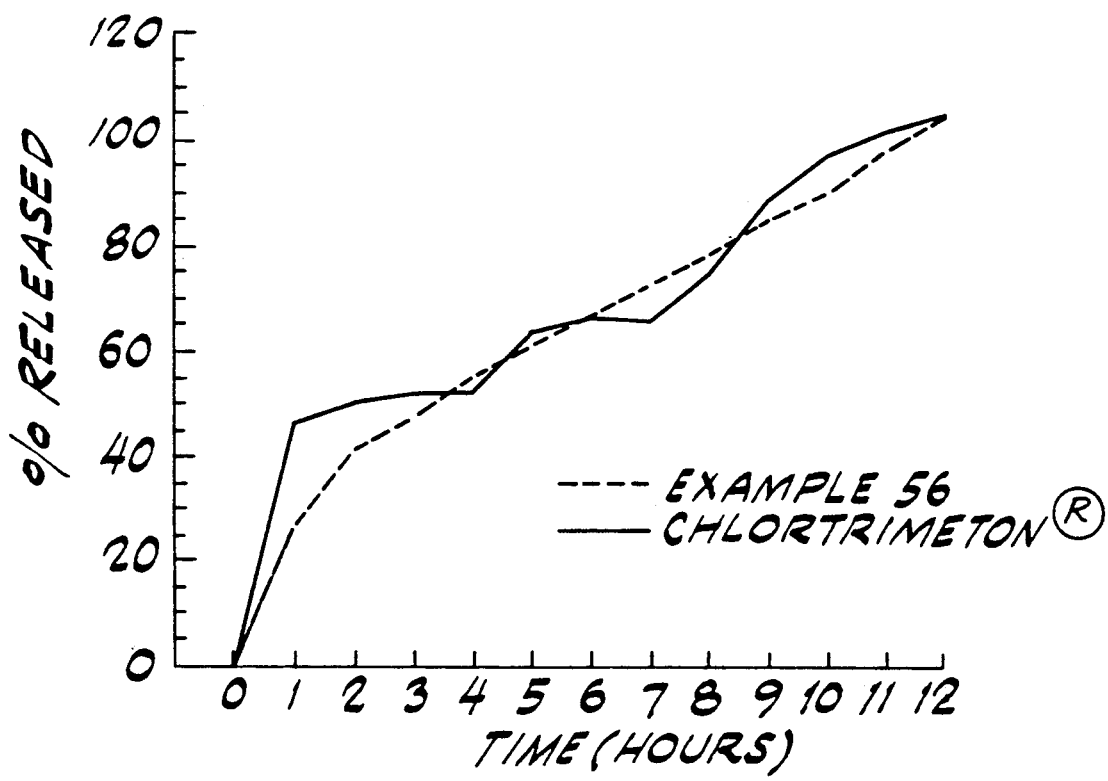
FIG. 13 is a graphical representation of the dissolution curves provided by Example 56 and Chlortrimeton®.

In Example 56, the excipient is blended with chlorpheniramine maleate and tableted according to the process set forth in Example 38. Each tablet weighs about 100 mg, and contains about 12 mg chlorpheniramine maleate, about 0.5 mg excipient, and about 87.5 mg excipient (containing 50% gums (XG:LBG in a 1:1 ratio). The tablets are then tested for dissolution in the same manner as Examples 41-43, and the dissolution curves compared to a similarly tested tablet of Chlortrimeton ® (a slow release formulation containing 12 mg chlorpheniramine maleate), available from Schering. The results are provided in FIG. 13.

Figure 14:
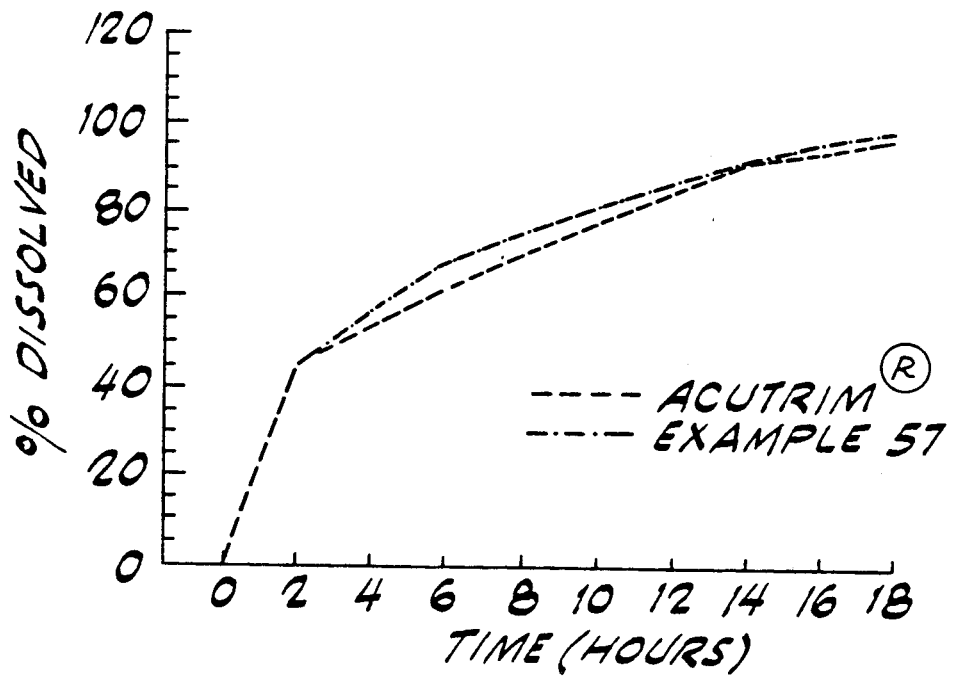
FIG. 14 is a graphical representation of the dissolution curves provided by Example 57 and Acutrim®.
Figure 15:
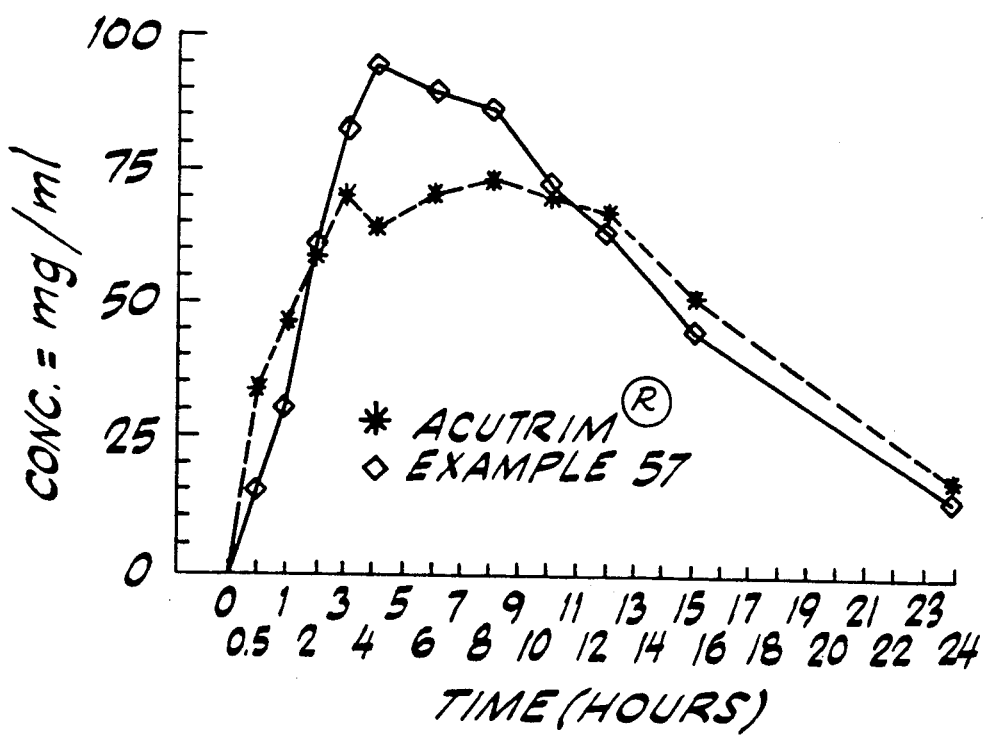
FIG. 15 is a graphical representation of the bioavailability of Example 57 as compared to Acutrim®.

In Example 57, the excipient is blended with phenylpropanolamine according to the process and tableted set forth in Example 38. Each tablet weighs about 845 mg, and contains about 75 mg phenylpropanolamine, 16.9 hydrogenated vegetable oil, 4.2 mg magnesium stearate, and 748.9 mg excipient (containing 50% gums (XG:LBG in a 1:1 ration). The tablets are then tested for dissolution in the same manner as Examples 41-43, and the dissolution curve compared to a similarly tested tablet of Acutrim ® (a slow release tablet containing 75 mg phenylpropanolamine), available from Ciba Consumer Products. The results are provided in FIG. 14. FIG. 15 is a graphical representation of the bioavailability of Example 57 as compared to Acutrim ®. The results are obtained in a two-way crossover study on six healthy male subjects (12 blood samples withdrawn and assayed for phenylpropanolamine in blood plasma).

As can be seen from the results obtained in Examples 54-57, the slow release excipient of the present invention is extremely versatile and readily provides formulations which can substantially match the dissolution curves of other slow release formulations.

The preceding theories are offered solely by way of explanation and it is not intended that the invention be limited to this theory.

The examples provided above are not meant to be exclusive. Many other variations of the present invention would be obvious to those skilled in the art, and are contemplated to be within the scope of the appended claims.

We claim:

1. A controlled release pharmaceutical excipient for use in oral solid dosage forms, comprising from about 20 to about 60 percent by weight of a hydrophilic material comprising xanthan gum and a galactomannan gum capable of cross-linking said xanthan gum in the presence of aqueous solutions, the ratio of said xanthan gum to said galactomannan gum being from about 3:1 to about 1:3, and from about 40 to about 80 percent by weight of an inert diluent selected from the group consisting of a monosaccharide, a disaccharide, a polyhydric alcohol, and mixtures thereof, the ratio of said inert diluent to said hydrophilic material being from about 4:1 to about 0.67:1.

2. A controlled-release tablet for absorption of an active medicament in the gastrointestinal tract, comprising a controlled-released excipient comprising a hydrophilic gum matrix comprising a xanthan gum and a galactomannan gum capable of cross-linking said xanthan gum when exposed to gastric fluid, the ratio of said xanthan gum to said galactomannan gum being from about 3:1 to doubt 1:3, and an inert diluent, the ratio of said inert diluent to said hydrophilic gum matrix being from about 4:1 to about 0.67:1, and an effective amount of a medicament to render a therapeutic effect, the ratio of said medicament to said hydrophilic gum matrix being from about 1:3 to about 1:10.

3. The excipient of claim 1, wherein said galactomannan comprises locust bean gum.

4. The excipient of claim 1, wherein said inert pharmaceutical filler comprises lactose, dextrose, sucrose, fructose, microcrystalline cellulose, xylitol, sorbitol or mixtures thereof.

5. The excipient of claim 1 to which an effective amount of a therapeutically active medicament is added.

6. The excipient of claim 1, wherein an effective amount of a therapeutically active medicament is added via dry granulation, yet granulation or a combination of dry and wet granulation and the resultant granulation is compressed to form solid tablets.

7. The excipient of claim 3, wherein said hydrophilic material further comprises one or more of tragacanth, acacia, karaya, alginates, agar, pectin, guar, hydroxypropyl guar, carrageenan, hydroxypropylmethyl cellulose, hydroxypropyl cellulose, methylcellulose, carboxymethyl cellulose, polyvinyl pyrollidone, and mixtures of any of the foregoing.

8. The excipient of claim 3, wherein said hydrophilic material further comprises propylene glycol alginate.

9. The excipient of claim 3, wherein said hydrophilic material further comprises a hydrocolloid, said hydrocolloid comprising up to about 50% by weight of said hydrophilic material.

10. The excipient of claim 1, wherein an effective amount of a therapeutically active medicament is added and the resulting mixture is encapsulated.

11. The excipient of to claim 1, wherein an effective amount of a therapeutically active ingredient is added and the resulting mixture provides a zero order controlled release when provided as a solid dosage form.

12. The excipient of claim 3, wherein said ratio of xanthan gum to locust bean gum is about 1:1.

13. A slow release pharmaceutical excipient, for use in solid oral dosage forms comprising a hydrophilic gum matrix comprising xanthan gum and locust bean gum in a ratio of about 3:1 to about 1:3; and an inert diluent, the ratio of said inert diluent to said hydrophilic gum matrix being from about 2.3:1 to about 1:1.

14. The tablet of claim 2, wherein said galactomannan gum is locust bean gum.

15. The tablet of claim 2, wherein said medicament is added to said excipient via dry granulation, wet granulation or a combination of dry and wet granulation.

16. A controlled release tablet for oral administration comprising (I) from about 20 to about 60 percent by weight of a hydrophilic material comprising from about 10 to doubt 90 percent of a heteropolysaccharide and from about 90 to about 10 percent of a cross-linking agent capable of cross-linking said heteropolysaccharide; and (II) up to about 80 percent of an inert pharmaceutical filler selected from the group consisting of a monosaccharide, a disaccharide, a polyhydric alcohol, and mixtures thereof, the ratio of said inert pharmaceutical filler to said hydrophilic material being from about 4:1 to about 0.67:1; and (III) an effective amount of a therapeutically active medicament to render a therapeutic effect.

17. The tablet of claim 16, wherein said heteropolysaccharide comprises xanthan gum and said cross-linking agent comprises a galactomannan.

18. The tablet of claim 17, wherein at least 3.5 hours ar required for 50 percent of said therapeutically active medicament to be released when said tablet is exposed to gastric fluid.

19. The tablet of claim 17, wherein said tablet provides a zero order controlled release of said therapeutically active medicament when said tablet is exposed to gastric fluid.

20. The tablet of claim 17, wherein said galactomannan comprises locust bean gum, and the ratio of xanthan gum to locust bean gum is about 1:1.

21. The tablet of claim 17, wherein said inert pharmaceutical filler comprises lactose, dextrose, sucrose, fructose, xylitol, sorbitol or mixtures thereof.

22. The tablet of claim 17, wherein said hydrophilic material further comprises a polysaccharide gum selected from the group consisting of tragacanth, acacia, karaya, alginates, agar, pectin, carrageenan, hydroxypropylmethyl cellulose, hydroxypropyl cellulose, methylcellulose, carboxymethyl cellulose, polyvinyl pyrollidone, and mixtures of any of the foregoing.

23. The tablet of claim 22, wherein said hydrophillic material further comprises propylene glycol alginate.

24. The tablet of claim 22, wherein said hydrophilic material further comprises a hydrocolloid.

* * * * *